United States Patent [19]

Kozlov et al.

[11] Patent Number: 4,988,622
[45] Date of Patent: Jan. 29, 1991

[54] RECOMBINANT PLASMID DNA PVN 22 CODING BIOSYNTHESIS OF HUMAN LEUKOCYTE INTERFERON ALPHA-I1 AND STRAIN PSEUDOMONAS SP. 31 (PVN 22) - PRODUCER OF HUMAN LEUKOCYTE INTERFERON ALPHA-I1 CONTAINING SAME

[76] Inventors: Jury I. Kozlov, ulitsa Golubinskaya, 7, korpus 2, kv. 178; Vera A. Nardoditskaya, ulitsa Generala Belova, 45, korpus 3, kv. 357, both of Moscow; Marina R. Eremashvili, prospekt Pshavela, II kvartal, korpus 23, kv. 24, Tbilisi; Alexander Y. Strongin, Sumskoi proezd, 2, korpus 4, kv. 21, Moscow; Viktor E. Sterkin, Sumskoi proezd. 2, korpus 1, kv. 496, Moscow; Marina A. Skvortsova, Starokonjushenny pereulok, 19, kv. 9, Moscow; Andrei J. Chistoserdov, poselok Mendeleeva, ultitsa Instutytskaya, 9, kv. 49, Moskovskaye oblast; Jury D. Tsygankov, ulitsa Generale Tjuleneva, 35, kv. 114, Moscow; Ljudmila V. Evdonina, Kolomensky proezd, 14, korpus 2, kv. 421, Moscow; Vitaly L. Jurin, Leningradsky prospekt, 78, korpus 4, kv. 21, Moscow; Galina S. Monastyrskaya, ulitsa Chertanovskaya, 29, korpus 1, kv. 126, Moscow; Evgeny D. Sverdlov, ulitsa Matveevskaya, 10, korpus 4, kv. 357, Moscow; Grigory M. Dolganov, ulitsa Miklukho-Maklaya, 51, korpus 1, kv. 248, Moscow; Sergei A. Tsarev, Novoyasenevsky prospekt, 19, korpus 4, kv. 326, Moscow, all of U.S.S.R.

[21] Appl. No.: 163,967
[22] PCT Filed: Apr. 29, 1987
[86] PCT No.: PCT/SU87/00052

§ 371 Date: Dec. 15, 1987
§ 102(e) Date: Dec. 15, 1987
[87] PCT Pub. No.: WO87/06613
PCT Pub. Date: Nov. 5, 1987

[30] Foreign Application Priority Data

Apr. 30, 1986 [SU] U.S.S.R. .................. 4065414

[51] Int. Cl.$^5$ .................. C12N 15/21; C12N 1/21; A61K 37/66
[52] U.S. Cl. .................. 435/252.34; 435/69.52; 435/172.3; 435/320.1; 424/85.7
[58] Field of Search .................. 424/85.4, 85.5, 85.6, 424/85.7; 435/68, 172.3, 252, 34, 320

[56] References Cited

U.S. PATENT DOCUMENTS 4,680,260 7/1987 Dehahov et al. .................. 435/68
4,748,233 5/1988 Sloma .................. 424/85.7

FOREIGN PATENT DOCUMENTS 0072541 2/1983 European Pat. Off. .

OTHER PUBLICATIONS

Nature vol. 287, 2 Oct. 1980.

Primary Examiner—Margaret Moskowitz
Assistant Examiner—Shelly J. Guest
Attorney, Agent, or Firm—Ladas & Parry

[57] ABSTRACT

A recombinant plasmid DVA pVN22 coding the biosynthesis of a human leukocyte interferon α-I1 having size of 10.85 t.p.b. and consisting of the following units:
EcoRI—HindIII—a fragment of the plasmid pAYC37 with the size of 9.45 t.p.b.,
HindIII—EcoRI—a fragment with the size of 1.4 t.p.b. consisting of the following members:
a fragment of DNA with the size of 0.25 t.p.b. with the regulatory range of gene D of the phague $\phi \times 174$ and the first codons of the gene of interferon
gene of interferon α-I1 with the size of 0.5 t.p.b.,
a region of the human genome DNA with the size of 0.65 t.p.b.;
it has the following genetic markers: genome Ap$^R$ en- (Abstract continued on next page.)

suring resistance against ampicillin, genome $Sm^R$ ensuring resistance to streptomycin; contains unique regions of recognition of restrictases: Hind III—O; EcoRI—1.4 t.p.b., BamHI—10.82 t.p.b., it is deposited at the collection of culture of microogranisms of the A11-Union Research Institute of Antibiotics and registered under the entry No. $1788^I$.

A strain Pseudomonas Sp. 31 (pVN22)—producer of a human leukocyte interferon α-I1 containing a recombinant plasmid DNA pVN22 produced by the method of genetic engineering by introducing said plasmid into bacteria of the genus Pseudomonas, deposited at the collection of cultures of microoorganisms of the A11-Union Research Institute of Antibiotics on 02.04.86 and registered under the entry No. 1788A.

2 Claims, 4 Drawing Sheets

RECOMBINANT PLASMID DNA PVN 22 CODING BIOSYNTHESIS OF HUMAN LEUKOCYTE INTERFERON ALPHA-I1 AND STRAIN PSEUDOMONAS SP. 31 (PVN 22) - PRODUCER OF HUMAN LEUKOCYTE INTERFERON ALPHA-I1 CONTAINING SAME

FIELD OF THE INVENTION

The present invention relates to the art of genetic engineering and biotechnology and, more particularly, to a novel in vitro engineered recombinant plasmid DNA pVN 22 coding the biosynthesis of human leukocyte interferon α-I1, and to a novel strain Pseudomonas sp. 31 (pVN 22) producing human leukocyte interferon α-I1 containing this plasmid.

PRIOR ART

Interferon—proteins produced by certain types of cells in response to viral infections, as well as in response to the effect of some other agents. Interferons exhibit an antiviral effect and a number of other properties: inhibition of cell growth, influence on their differentiation, activation of macrophages, increasing the number of antibody-independent killer cells, and the like. Interferons produced by human leukocytes are referred to as leukocyte interferons (interferons α) and comprise a family of related proteins containing 166 (in one case 165) aminoacid moieties. The homology of the aminoacid sequences for different interferons α is as high as 80% and over. Every kind of interferon α is coded by its own gene and after induction of the synthesis of interferons by a corresponding agent a mixture of interferons α is delivered into the blood plasma. The biological activity of different interferons α determined by their ability of protecting cells from the effect of viruses considerably varies; their other biological and physico-chemical properties are also different. In the preparation of interferons α for pharmaceutical purposes donor's blood is conventionally employed. However, this source is not capable of fully meeting the demand in high-purity interferons. The use of bacterial producers-strains created by methods of molecular cloning and genetic engineering enables preparation of interferons α in substantially any required amounts. However, every individual producer gives only one kind of interferon α out of a great number thereof. To obtain a pharmaceutical preparation having properties close to those of a natural compound, it is necessary to be in possession of a whole range of producers synthesizing various kinds of interferons α (e.g., α-A, α-B, α-C, α-1 and the like), so that a high-purity interferons α could be further intermixed in such proportions that usually prevail in the human blood. Sufficiently active bacterial producers of some subtypes of interferons α have already been prepared by methods of the genetic engineering. Thus, engineered were recombinant plasmids ensuring biosynthesis of interferons α-A, α-F, α-K and others in cells of E. coli. However, this is not sufficient for obtaining preparations fully reproducing the effect of a mixture of interferons α obtained from the donor's blood.

Known in the art is a recombinant plasmid DNA pLeIF-rL synthesized on the basis of the vector pBR 322 and coding the biosynthesis of interferon α-L; also known is the strain Escherichia coli 294 containing this plasmid (EPA2 0072541). The gene of interferon α-L is prepared from the library of human genes using the phague λ Haron 4A. In the plasmid pLeIF-rL the synthesis of interferon α-L is controlled by an inducible tryptophane promotor.

This strain is characterized by that during its fermentation on enriched media with a relatively high content of tryptophane (LB-medium, Hottinger's broth) usually employed for ensuring a rapid growth of bacteria, a low level of biosynthesis of the desired product is observed. This disadvantage is connected with the fact that the synthesis of interferon α-L is effected under control of the regulatory area of the tryptophane promotor the operation of which must be induced. To obtain a high level of biosynthesis of interferon α-L, the cultural broth should be diluted with a minimal salt medium by 20-40 times. A considerable decrease of tryptophane concentration in the medium results in normalization of transcription of the gene and in intensification of the synthesis of interferon by 20-50 times. In a commercial scale production such dilution of a growing culture is very difficult, the more so that a strict sterility should be observed during the dilution in order to avoid phagolysis of the culture E. coli. Furthermore, E. coli—conditionally pathogenic microorganism and its use in the production is undesirable.

DISCLOSURE OF THE INVENTION

Figure 1:
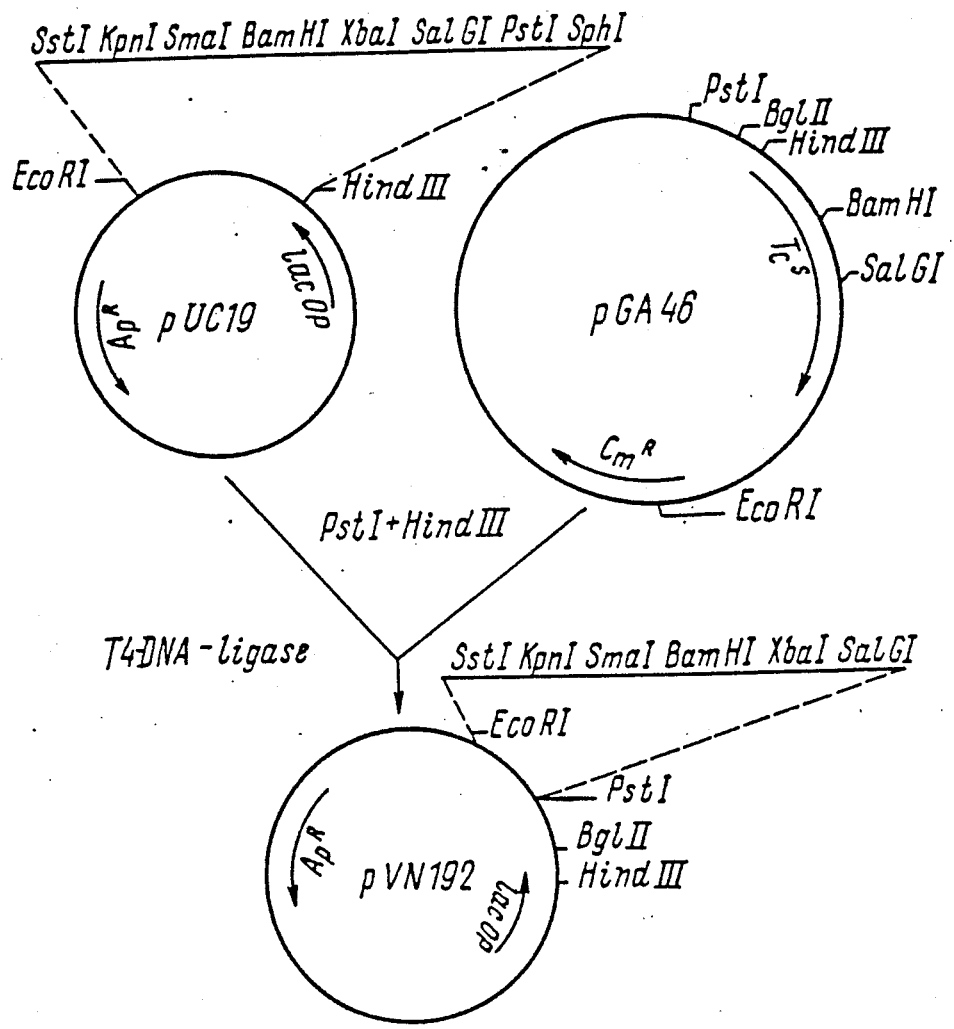
FIG. 1 shows a chart for the preparation of plasmid p VN 192.

The recombinant plasmid DNA pVN22 and the strain Pseudomonas sp.31 (pVN22) - producer of leukocyte interferon α-I1 are novel and hitherto unknown from the literature.

The present invention is directed to the provision of a novel recombinant plasmid DNA coding the biosynthesis of human leukocyte interferon α-I1 and a novel strain - producer of interferon α-I1 containing the same and ensuring preparation of leukocyte interferon α-I1 in a high yield.

This object is accomplished by that the recombinant plasmid DNA pVN22 coding the biosynthesis of human leukocyte interferon α-I1 according to the present invention has the size of 10.85 t.p.b. (thousands pairs of bases) and consists of the following units:

EcoRI - Hind III - fragment of the plasmid pAYC 37 with the size of 9.45 t.p.b.;

Hind III - EcoRI - fragment with the size of 14 p.o.b. consisting of the following members:

DNA fragment of 0.25 t.p.b. size with the regulatory range of the gene D of phague λ×174 and the first codons of the gene of interferon α;

gene of interferon α-I1 of 0.5 t.p.b. size;

region of a human genome DNA of 0.65 t.p.b. size;

The above-mentioned recombinant plasmid DNA has the following genetic markers: gene $Ap^R$ ensuring resistance to amplicillin; genome $Sm^R$ ensuring resistance to streptomycin; it contains the following unique regions of recognition of restrictases: Hind III-O, EcoRI - 1.4 t.p.b., BamHI - 10.82 t.p.b.; it is deposited at the collection of cultures of microorganisms of the All-Union Research Institute of Antibiotics and registered under the entry No. 1788A1.

The plasmid according to the present invention is capable of being replicated in various gram-negative bacteria such as *E. coli*, Pseudomonas and the like and it ensures the biosynthesis of human leukocyte interferon α-I1 which differs from the known interferon α-1 by three aminoacid substituents in the positions 34; 55; 161.

The gene of interferon α-I1 incorporated in the plasmid according to the present invention and having the size of 0.50 t.p.b. is of the following structure:

| Start | | | | | | | | | | | |
|---|---|---|---|---|---|---|---|---|---|---|---|
| Met | Cys | Asp | Leu | Pro | Gln | Thr | His | Ser | Leu | Gly | 10 |
| ATG | TGT | GAT | CTG | CCT | CAG | ACC | CAC | AGC | CTG | GGT | |
| | Asn | Arg | Arg | Ala | Leu | Ile | Leu | Leu | Ala | Gln | 20 |
| | AAT | AGG | AGG | GCC | TTG | ATA | CTC | CTG | GCA | CAA | |
| | Met | Gly | Arg | Ile | Ser | Pro | Phe | Ser | Cys | Leu | 30 |
| | ATG | GGA | AGA | ATC | TCT | CCT | TTC | TCC | TGC | CTG | |
| | Lys | Asp | Arg | His | Asp | Phe | Gly | Leu | Pre | Gln | 40 |
| | AAG | GAC | AGA | CAT | GAC | TTT | GGA | CTT | CCC | CAG | |
| | Glu | Glu | Phe | Asp | Gly | Asn | Gln | Phe | Gln | Lys | 50 |
| | GAG | GAG | TTT | GAT | GGC | AAC | CAG | TTC | CAG | AAG | |
| | Thr | Gln | Ala | Ile | Pro | Val | Leu | His | Glu | Met | 60 |
| | ACT | CAA | GCC | ATC | CCT | GTC | CTC | CAT | GAG | ATG | |
| | Ile | Gln | Gln | Thr | Phe | Asn | Leu | Phe | Ser | Thr | 70 |
| | ATC | CAG | CAG | ACC | TTC | AAT | CTC | TTC | AGC | ACA | |
| | Glu | Asp | Ser | Ser | Ala | Ala | Trp | Glu | Gln | Ser | 80 |
| | GAG | GAC | TCA | TCT | GCT | GCT | TGG | GAA | CAG | AGG | |
| | Leu | Leu | Glu | Tys | Phe | Ser | Thr | Glu | Leu | Tyr | 90 |
| | CTC | CTA | CAA | AAA | TTT | TCC | ACT | GAA | CTT | TAC | |
| | Gln | Gln | Leu | Asn | Asn | Leu | Glu | Ala | Cys | Val | 100 |
| | CAG | CAA | CTG | AAT | AAC | CTG | GAA | GCA | TGT | GTG | |
| | Ile | Gln | Glu | Val | Gly | Met | Glu | Glu | Thr | Pro | 110 |
| | ATA | GAG | GAG | GTT | GGG | ATG | GAA | GAG | ACT | CCC | |
| | Leu | Met | Ash | Glu | Asp | Ser | Ile | Leu | Ala | Val | 120 |
| | CTG | ATG | AAT | GAG | GAC | TCC | ATC | CTG | GCT | GTG | |
| | Arg | Lys | Tyr | Phe | Gln | Arg | Ile | Thr | Leu | Tyr | 130 |
| | AGG | AAA | TAC | TTC | CAA | AGA | ATC | ACT | CTT | TAT | |
| | Leu | Thr | Glu | Lys | Lys | Tyr | Ser | Pro | Cys | Ala | 140 |
| | CTA | ACA | GAG | AAG | AAA | TAC | AGC | CCT | TGT | GCC | |
| | Trp | Glu | Val | Val | Arg | Ala | Glu | Ile | Met | Arg | 150 |
| | TGG | GAG | GTT | GTC | AGA | GCA | GAA | ATC | ATG | AGA | |
| | Ser | Leu | Ser | Phe | Ser | Thr | Asn | Leu | Gln | Lys | 160 |
| | TCC | CTC | TCT | TTT | TCA | ACA | AAC | TTG | CAA | AAA | |
| | Arg | Leu | Arg | Arg | Lys | Asp | | | | | |
| | AGA | TTA | AGG | AGG | AAG | GAT | TGA | | | | |

The present invention also relates to a novel strain Pseudomonas sp. 31 (pVN 22)—producer of a human leukocyte interferon α-I1 containing the above-specified recombinant plasmid DNA pVN22. The strain according to the present invention produced by methods of genetic engineering by way of introduction of the recombinant plasmid DNA pVN22 into bacteria of the genus Pseudomonas was deposited on 02.04.86 at the collection of cultures of microorganisms of the All-Union Research Institute of Antibiotics and registered under the entry No. 1788A.

In contrast to the known plasmid pLeIF-rL wherein the synthesis is controlled by an inducible promotor, in the plasmid pVN22 according to the present invention the synthesis of interferon α-I1 is controlled by a constitutive promotor of the gene D of the phague $\phi \times 174$ which simplifies the fermentation process. The use, as the vector, of the plasmid pAYC37 (Tsygankov Y. D., Christoserdov A. Y., Plasmid I.Y., 118–125, 1985) with a broad spectrum of hosts increases stability of the recombinant plasmid according to the present invention pVN22 produced on its basis, in contrast to the less stable vector pBR322 employed for the preparation of the known plasmid. The plasmid pVN22 according to the present invention can be rather stably maintained in various strains even without the addition of antibiotics to the cultural medium, whereas the prior art plasmid pLeIF-rL prepared on the basis of pBR 322 is rather rapidly eliminated under such conditions. The use, as a producer, of the strain Pseudomonas sp. 31 (pVN22) according to the present invention makes it possible to increase activity of interferon α-I1 to $0.7-2.5 \times 10^9$ MU/1 of cultural liquid. The use of the strain according to the present invention for the synthesis of interferon α-I1 considerably lowers the possibility of phagolysis during the fermentation process. Furthermore, the strain according to the present invention, in contrast to strains of *E. coli*, is not a conditionally pathogenic microorganism. Therefore, the use of the present invention makes it possible to obtain human leukocyte interferon α-I1 in a high yield by a simple production process.

BEST MODE FOR CARRYING OUT THE INVENTION

The method for engineering the recombinant plasmid DNA pVN22 according to the present invention consists in the following steps.

The plasmid vector pAYC37 capable of being maintained in gram-negative bacteria is cleaved by means of restrictases Hind III and EcoRI and also by means of a DNA-ligase a Hind III-Ecor I fragment with the size of 1.4 t.p.b. is introduced in which fragment a gene of interferon α-I1 is located which is under control of a promotor of the gene D of the phague $\phi \times 174$.

The above-specified Hind-III-Ecor I fragment of the size of 1.4 t.p.b. consists of the following units:
DNA fragment of 1.25 t.p.b. size with the regulatory field of the gene D of the phague $\phi \times 174$ and the first codons of the gene of interferon α,
gene of interferon α-I1 of 0.5 t.p.b. size, region of a human genome DNA of 0.65 t.p.b. size; the above-specified plasmid recombinant DNA has genetic markers: gene $Ap^R$ ensuring resistance against ampicillin, gene $Sm^R$ ensuring resistance against streptomycin; it contains the following unique portions of recognition of restrictases: Hind III-O, Ecor I - 1.4 t.p.b., Bam HI - 10.82 t.p.b.

The obtained recombinant plasmids are introduced, by transformation, into different strains *E. coli*, such as *E. coli* K802 and C600. The selection of the transformants is effected according to the appearance of resistance to ampicillin and streptomycin in them, the gene $Sm^R$ in this case is transcribed from the promotor of the gene D of the phague $\phi \times 174$. Such transformants synthesize interferon α-I1 possessing a biological activity in considerable amounts. In this manner the strain *E. coli* C600 was obtained which contains a plasmid denominated pVN22. The strain *E. coli* C600 (pVN22) synthesizes interferon α-I1 with the activity of up to $1 \times 10^8$ MU/1. The plasmid pVN22 is capable of a mobilization transfer by means of conjugative plasmids. For mobilization of pVN22 the plasmid R751 ensuring resistance of trimetaprim is introduced into the strain *E. coli* C600 (pVN22) by conjugation. Thereafter an interspecies conjugation is effected between *E. coli* C600 (pVN22, R751) and Pseudomonas sp. 31. The mixture of the bacteria is inoculated into dishes with the minimal Adams salt medium containing ampicillin, streptomycin, and the aminoacid threonine and is cultured at the temperature of 30° C. Under such conditions only cells of Pseudomonas sp. 31 (R751, pVN22) do grow, since for the growth of the donor strain *E. coli* C600 (R751, pVN22) leucine is also necessary in addition to threonine. In a further work trimetaprim is not added to the medium wherein the strain Pseudomonas sp. 31 (pVN22), since the presence of the plasmid R751 is not obligatory for the producing strain.

The strain Pseudomonas sp. 31 (pVN22) ensures a high level of biosynthesis of interferon α-I1 which is as high as $2.5 \times 10^9$ MU/1 of the cultural liquid.

The strain Pseudomonas sp. 31 (pVN22) according to the present invention producing human leukocyte interferon α-I1 is characterized by the following features.

Morphological features. Cells straight, bacilliform, of 3–5 μ length, gram-negative, non-sporiferous.

Cultural features. Cells grow well on simple nutrient media. On a meat-peptone agar after 24 hours of growth at a temperature of 25°–30° C. they form large colonies with an uneven edge (3–4 mm in diameter), the surface is rough, of light-green colour. A uniform slime is formed upon growing on the Hottinger broth or in the liquid medium M9. After 24 hours of growth on the Hottinger broth with aeration the culture acquires a light-green colour and becomes slightly opalescent.

Physiological and biochemical features. Cells of Pseudomonas sp. 31 (pVN22) grow at a temperature within the range of from 10° to 35° C. with the optimum at 30° C. at a pH of from 6.7 to 7.5. Sources of carbon: glucose, arabinose. Sources of nitrogen: ammonium salts, urea; also used may be aminoacids, peptone, tryptone and the like.

Resistance to antibiotics. Cells of Pseudomonas sp. 31 (pVN22) are resistant to 400–500 μg/ml of streptomycin and 150–200 μg/ml of ampicillin.

The plasmid is stable in the strain Pseudomonas sp. 31 (pVN22) upon upkeeping the cells of Pseudomonas sp. 31 (pVN22) for 6 months on an agarized medium containing ampicillin and streptomycin in corresponding concentrations; no losses or rearrangement of the plasmid is observed.

For better understanding of the present invention the following examples illustrating the modes of engineering of the recombinant plasmid DNA pVN22 and preparation of the strain according to the present invention are given hereinbelow.

EXAMPLE 1

For engineering of the recombinant plasmid DNA pVN22 according to the present invention use is made of fragments of the plasmid pAYC37 and plasmid pVN609 according to the following scheme.

Two intermediate plasmids pVN192 and pVN61 are preliminary prepared, whereafter engineering of the plasmid pVN609 is carried out.

The procedure of engineering of the plasmid pVN192 is shown by way of illustration in FIG. 1 of the drawing attached.

0.1 μg of DNA of the plasmid pUC19 and 1 μg of the plasmid pGA46 are cleaved by means of the restrictases PstI and Hind III under the following conditions: 6 mM of Tris-HCl, pH 7.6, 6 mM of 2-mercaptoethanol and 50 mM NaCl, PstI - 1 activity unit, Hind III - 1 activity unit, the reaction mixture volume is 20 μl. The reaction is carried out for one hour at the temperature of 37° C. and stopped by heating for 20 minutes at the temperature of 65° C. Then the ligation of the resulting fragments is effected by means of the DNA-ligase of the phague T4 under the following conditions: 60 mM of Tris-HCl, pH 7.6, 10 mM $MgCl_2$, 10 mM of 2-mercaptoethanol, 0.4 mM of adenosinetriphosphoric acid, DNA-ligase - 2 activity units, the reaction mixture volume - 25 μl. The ligation is conducted at a temperature of 12°–14° C. for 90 minutes, whereafter such a mixture is introduced into cells of *E. coli* JM 83 by transformation. The transformation is conducted in the following manner: an overnight culture of *E. coli* JM 83 is diluted by 500 times with the liquid medium LB and cultured under aeration at the temperature of 37° C. till the cell culture attains an optimal density at 550 nm of 0.4–0.6 unit, whereafter the cells are cooled on an ice bath and all the subsequent operations are carried out at a temperature of 2°–4° C.; 10 ml of the cooled cell suspension are centrifuged, the supernatant is thoroughly removed and the cells are suspended in 10 ml of a 0.1M $CaCl_2$ at a temperature of 2°–4° C. and maintained for 30 minutes; then the cells are collected by centrifugation and resuspended in 0.5 ml of a 0.1M of $CaCl^2$; to 100 μl of the thus-prepared cells 25 μl of a solution of DNA are added after ligation; the cell suspension in a 0.1M $CaCl^2$ and the added DNA solution are thoroughly intermixed and allowed to stand for 30 minutes at a temperature of 2°–4° C., then heated at the temperature of 42° C. for 4–5 minutes, whereafter again placed on an ice bath for 20 minutes; then the suspension is diluted by 10 times with the medium LB and placed for 30 minutes into a thermostat at the temperature of 37° C.; after a short-time growing 50–100 μl of the cell suspension are inoculated into dishes with a selective medium. The selective medium upon selection of the transformants obtained in cloning of the fragments on the plasmid pUC19 obtains the following components; α-agar, ampicillin - 100 μg/ml, isopropylthiogalactosid - 10 mM, 5-bromo-4-chloro-3-indolyl-D-β-galactosid - 40 μg/ml. Non-coloured colonies are selected. Blue-coloured colonies bear the vector pUC19 reduced as a result of the ligation. The plasmid DNA is recovered from non-coloured colonies by the Birnboim and Dolly method and those plasmids where the recognition unit BgIII appears are selected. The restriction reaction is conducted in a manner similar to that described hereinbefore; its results are analyzed by electrophoresis of DNA in a 1% agarose gel in a tris-borate buffer (0.1M Tris-borate, 0.1M boric acid, 0.002M sodium ethylenediamine tetraacetate), followed by coloration of the gel with ethydium bromide so as to enable visualization of DNA in a long-wave UV spectrum. All the colonies analyzed in this manner contained the plasmid DNA with the recognition unit BgIII thereinside. In this manner the vector plasmid pVN192 was obtained which contained single recognition units of the following restrictases: HindIII, BlgII, Pst from PstI to EcoRI (contains polylinker succession from pUC 19).

Figure 2:
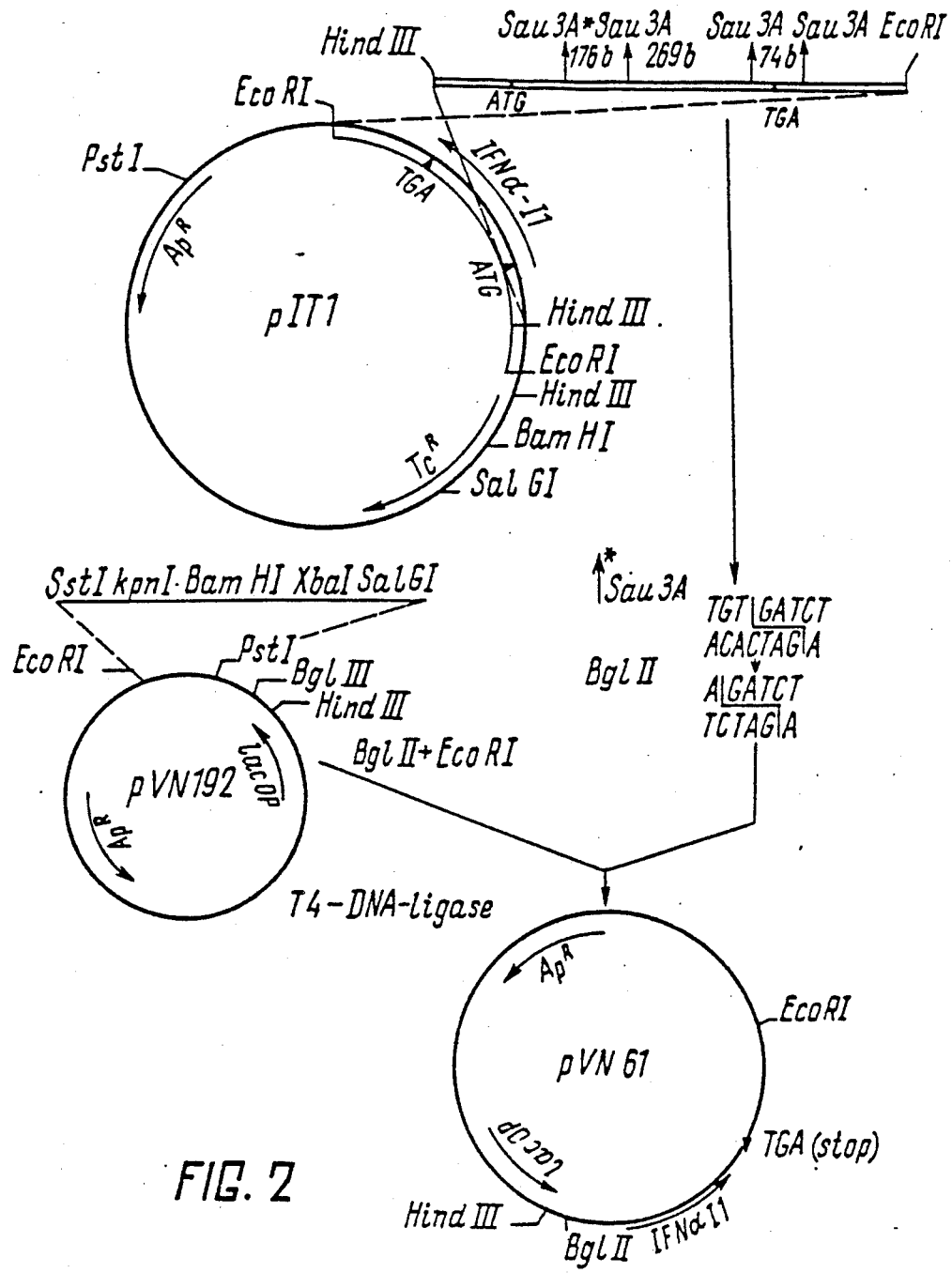
FIG. 2 shows a chart for the preparation of plasmid p VN 61.

Then the plasmid pVN 61 (FIG. 2) is engineered. 30 μg of the plasmid p T 1 are cleaved by means of restrictases HindIII and EcorRI under the following conditions: t mM Tris-HCl, pH 7.6, 6 mM $MgCl_2$, 6 mM of 2-mercaptoethanol and 50 mM NaCl; EcOR and Hind III—30 activity units, $H_2O$— to 1 ml. The reaction is carried out for 2 hours under slow stirring at the temperature of 37° C. and is stopped by heating at the temperature of 65° C. for 20 minutes. The completeness of cleavage of DNA is checked by electrophoresis of DNA in a 1% agarose gel in a manner similar to that described hereinabove. After checking, the remaining DNA is deposited on a 1% agarose gel and the fragments are divided electrophoretically. Then the required fragment is obtained by electroelution. The resulting fragment is subjected to a restricted hydrolysis by means of the restrictase Sau3A. To this end, the enzyme is diluted by means of an incubation buffer. Into each sample containing 0.5 mg of the pure fragment 0.1 activity unit of Sau3A is added and the time is selected during which the fragment is cleaved only partly (incubation is conducted for 2 min, 4 min, 6 min and so forth). The reaction is stopped by placing the samples into a water thermostat with the temperature of 68° C. for 20 minutes. The cleavage completeness is controlled by means of electrophoresis in an ultra-fine gel which enables application of only ¼ of the volume of the entire sample. The resulting fragments are built-in into the plasmid pVN192 treated by the restrictases BgIII and EcoRI. To this end, DNA of pVN192(2 μg) is cleaved by means of the restrictases Bgl II and EcoRI under the following conditions: 100 mm of Tris-HCl, pH 7.5, 6 mM $MgCl_2$, 6 mM of 2-mercaptoethanol, 50 mM NaCl), EcoRI—2 activity units, HindIII—2 activity units, $H_2O$— to 30 μl. The reaction is conducted for one hour at the temperature of 37° C. and stopped by placing the samples into a thermostat with the temperature of 65° C. Then ligation is conducted using DNA-ligase of the phague T4 cleaved at Bgl II and EcoRI, DNA pVN192 with the cleaved, by Sau3A, DNA HindIII-EcoRI fragment from p|T I. The reaction is conducted in a manner similar to that described hereinbefore, the DNA content: 0.1 μg pVN192, 0.4 μg of the DNA fragment, the final volume 20 μg. The resulting mixture is introduced by transformation into E. coli JM 83 and the cells are inoculated onto an agarized medium containing 100 μg/ml of ampicillin.

Figure 3:
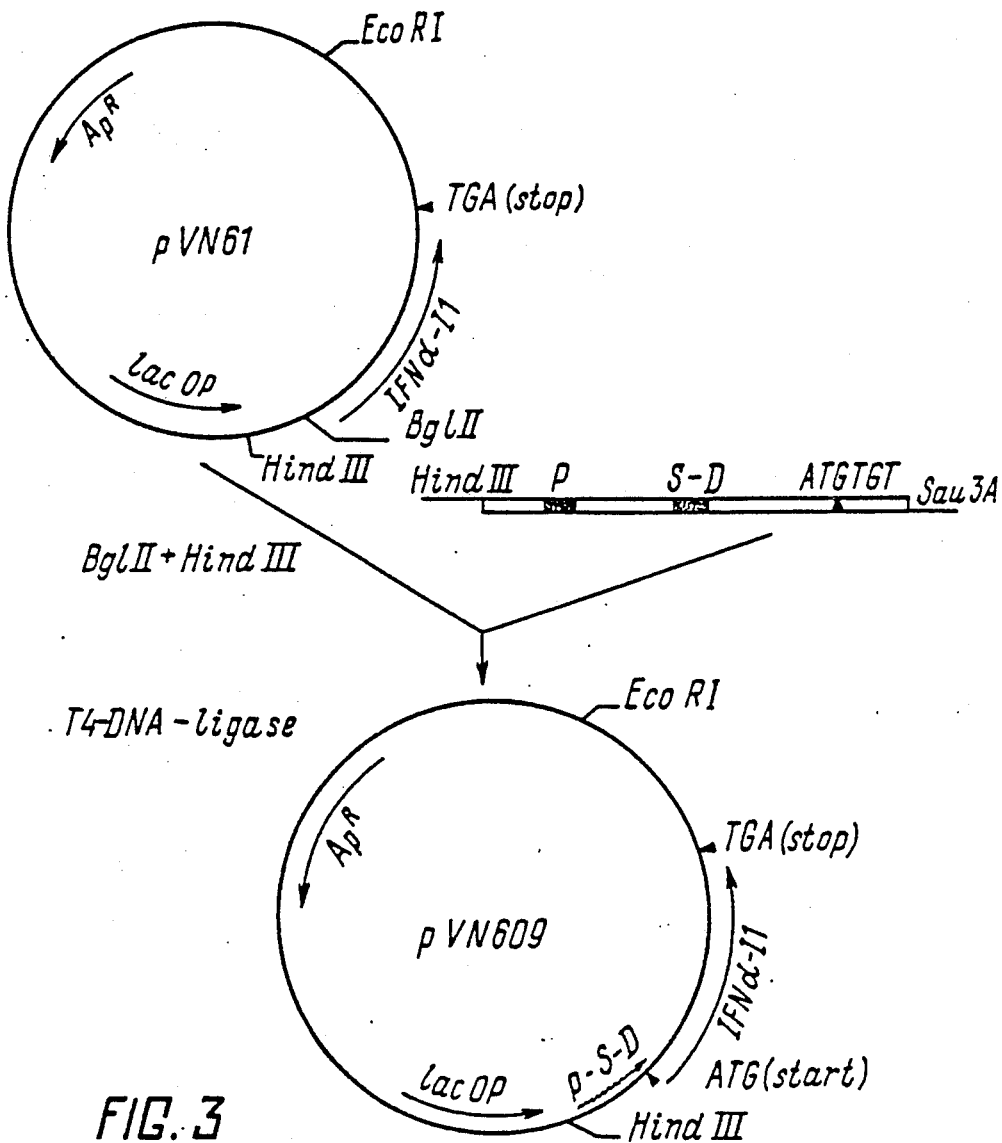
FIG. 3 shows a chart for the preparation of plasmid p VN 609.

The search for clones with fragments of the gene of interferon is carried out by the in situ hybridization method. To this end, colonies are grown on nitrocellulose filters, pore size of 0.45 μm. Then the colonies on the filters are subjected to lysis and hybridization is conducted using a labeled $\times 32$ p probe comprising a unit of the gene of interferon α-A. This is possible, since DNA of the gene of interferon α-A has a nucleotide order (succession) similar to that of the gene of interferon α-I1. The hybridizing colonies are revealed by means of radioautography. From the clones which are hybridized with the probe the plasmid DNA is recovered and by means of the restriction analysis those plasmids are revealed which contain the recognition unit Bgl II. In this manner the plasmid pVN61 is obtained. Then the plasmid pVN609 is engineered (FIG. 3). 0.1 μg of Hind III-Sau3A fragment of DNA of 0.25 t.p.b. size with the promotor of gene D of the phague $\phi \times 174$, S-D—succession of gene D, as well as ATG and TGT—codons of a mature gene of interferon α-A are enzymatically ligated with 0.5 μg of DNA pVN61 preliminarily cleaved by the restrictases HindIII and Bgl II under the conditions similar to those described hereinbefore.

Then the mixture resulting from the ligation is introduced, by transformation, into E. coli JM 83 and the biological activity of interferon α-I1 is determined in the transformants. In this manner the clone containing the plasmid pVN609 is identified which plasmid ensures the synthesis of mature interferon α-I1 in cells E. coli under the control of the promotor of gene D of the phague $\phi - 174$.

Figure 4:
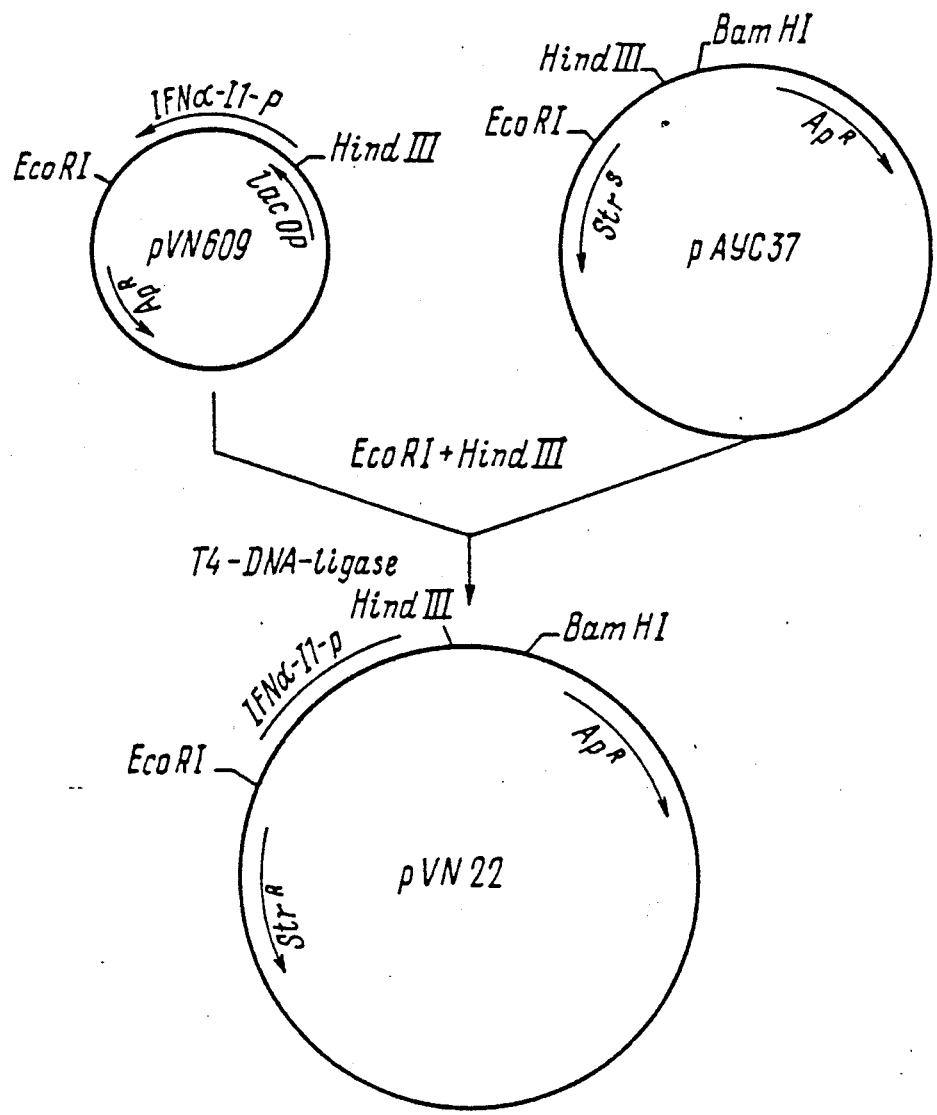
FIG. 4 shows a chart for the preparation of plasmid p VN 22.

Then the plasmid pVN22 is engineered (FIG. 4). 0.2 μg of DNA of the plasmid pAYC37 and 1 μg of DNA of the plasmid pVN609 are cleaved by means of the restrictases EcoRI and HindIII under the following conditions: 6 mM Tris-HCl, pH 7.6, 6 mM $MgCl_2$; 6 mM of 2-mercaptoethanol and 50 mM NaCl; EcoRI—2 activity units, Hind III—2 activity units; volume of the reaction mixture—30 μl. The reaction is conducted for 40 minutes at the temperature of 37° C. and stopped by heating for 15 minutes at the temperature of 65° C. Then the obtained fragments are ligated by means of DNA-ligase of the phague T4. The ligation is conducted at the temperature of 12°-14° C. for 120 minutes, whereafter this mixture is introduced into E. coli C600 by transformation. The transformed cells after a longtime foregrowing (2.5 hours) are inoculated onto the agarized LB medium containing, as selective markers, streptomycin (100 μg/ml). The vector plasmid pAYC37 is not capable of giving transformants on such medium upon reduction, since it has no resistance against streptomycin. The promotor responsible for expression of the streptomycin-resistance is absent in pAYC37. Upon cloning of the promotor-containing fragment with interferon αI1 from pVN609 into pAYC37 there occurs the reduction of resistance to streptomycin which enables an easy selection of clones containing the required plasmids. From such clones the plasmid DNA is recovered and the plasmid structure is checked by means of restrictases Hind III and EcoRI under conditions similar to those described hereinabove. The analysis of the obtained fragments is effected by means of electrophoresis in a 1% agarose gel in a standard Tris-borate buffer, followed by coloration of the gel by ethydium bromide. In this manner the plasmid pVN22 has been identified.

EXAMPLE 2

Preparation of the strain Pseudomonas sp. 31 (pVN22) producing interferon αI1 is effected in the following manner. For the introduction of the plasmid pVN22 into Pseudomonas sp. 31 two successive conjugations are employed. First of all, into the strain E. coli C600 (pVN22) the plasmid R751 is introduced by conjugation. The plasmid R751 ensures resistance against trimetaprim.

The inoculation of the conjugants is effected onto a minimal agarized Adams salt medium containing the following components; glucose 4 mg/ml, thiaminehydrochloride 5 µg/ml, threonine 50 µg/ml, leucine 50 µg/ml, ampicillin 75 µg/ml, streptomycin 75 µg/ml, trimetaprim (75 µg/ml). Under these conditions only conjugants of E. coli C 600 do grow (R 751, pVN22). Then the conjugation is carried out between E. coli C 600 (R 751, pVN22) and Pseudomonas sp. 31 is effected with a defective gene thr A. The conjugants grow on a minimal agarized salt medium of the following composition: glucose 4 mg/ml, thiaminehydrochloride 5 µg/ml, threonine 50 µg/ml, ampicillin 75 µg/ml, streptomycin 200 µg/ml, trimetaprim 75 µm/ml. The growth temperature of the conjugants is 30° C. The strain-donor of E. coli C600 (R 751, pVN22) needs, in addition to threonine, leucine as well, wherefore it does not grow on such medium. As a result, the strain Pseudomonas sp. 31 (pVN22) is obtained which contains the plasmid ensuring the synthesis of interferon α-Il with the activity of 0.7 to $2.5 \times 10^9$ MU/l.

EXAMPLE 3

Culturing of the strain Pseudomonas sp. 31 (pVN22) is effected by growing at the temperature of 28° C. for 14 hours on a slant agarized standard Hottinger medium containing antibiotics ampicillin (75 µg/ml), streptomycin (150 µg/ml). Trimetaprim is not added to the medium, since the presence of the plasmid R 751 does not affect the production of interferon. The biomass grown on the slants is used for the preparation of an inoculation material. To this end, the cells are transferred into 750 ml Erlenmeyer flasks with 100 ml of the abovementioned medium, but without agar and are grown in a shaker under stirring (240 r.p.m.) for several hours at the temperature of 28° C. The optical density of the inoculation culture should be equal to about 1-2.5 units at 550 nm. The fermentation is carried out in a fermenter equipped with systems for control of temperature, pH, stirring speed and aeration rate, as well as with a sensor of partial pressure of dissolved oxygen. The inoculation culture is introduced in the amount of 5% by volume into the fermenter with the above-specified medium. The cells are grown to an optical density (under standard conditions) of 2-4 units at a pH=6.7-6.9 and at the temperature of 28°±0.5° C. The process is conducted under intensive aeration and stirring. The aeration and stirring conditions are chosen so that the growth of the culture would not be limited by the concentration of dissolved oxygen wherefor the value of the partial pressure of oxygen is maintained at the level of 5-10% of saturation.

For stabilization of the pH use is made of ammonia water. The biomass growth is controlled by variation of the optical density of the cultural medium. On completion of the fermentation the activity of interferon is equal to $1.2 \times 10^9$ MU/l.

INDUSTRIAL APPLICABILITY

The recombinant plasmid DNA pVN22 coding the biosynthesis of human leukocyte interferon α-Il according to the present invention is useful in the preparation of strains- producers of human leukocyte interferon α-Il with a high activity.

The strain Pseudomonas sp. 31 (pVN22)—α-Il according to the present invention—producer of human leukocyte interferon is useful in the microbiological and medical industries for the preparation of interferon α-Il which can be employed in medical practice both in combination with other known leukocyte interferons and individually.

We claim:

1. A recombinant plasmid DNA pVN22 coding the biosynthesis of a human leukocyte interferon α-Il, characterized in that it has the size of 10.85 t.p.b. and consists of the following units:
   EcoRI—HindIII—a fragment of the plasmid pAYC37 with the size of 9.45 t.p.b.,
   HindIII—EcoRI—a fragment of 1.4 t.p.b. size consisting of the following units:
   a fragment of DNA of 0.25 t.p.b. size with the regulatory field of the gene D of the phague φ×174 and the first codons of the gene of interferon α,
   gene of interferon α-Il of 0.5 t.p.b. size,
   a region of a human genome DNA of 0.65 t.p.b. size;
   said recombinant plasmid DNA has the following genetic markers: genome $Ap^R$ ensuring resistance against ampicillin, genome $Sm^R$ ensuring resistance against streptomycin; contains the following unique regions of recognition of restrictases: HindIII-O; EcoRI—1.4 t.p.b., Bam HI - 10.82 t.p.b. deposited at the collection of cultures of microorganisms of the All-Union Research Institute of Antibiotics and registered under the entry No. 1788A.$^I$ 2. A strain Pseudomonas sp. 31 (pVN22)—producer of human leukocyte interferon α-Il containing recombinant plasmid DNA pVN22 according to claim 1, produced by the method of genetic engineering by introducing recombinant plasmid DNA pVN22 into bacteria of the genus Pseudomonas deposited on 0.2.04.86 at the collection of cultures of microorganisms of the All-Union Research Institute of Antibiotics and registered under the entry No. 1788A.

* * * * *